United States Patent
Sikora et al.

(10) Patent No.: US 12,185,954 B2
(45) Date of Patent: *Jan. 7, 2025

(54) GLENOID RESURFACING SYSTEM AND METHOD

(71) Applicant: Arthrosurface Incorporated, Franklin, MA (US)

(72) Inventors: George Sikora, Bridgewater, MA (US); Steven W. Ek, Durham, NH (US)

(73) Assignee: ARTHROSURFACE INCORPORATED, Franklin, MA (US)

( * ) Notice: Subject to any disclaimer, the term of this patent is extended or adjusted under 35 U.S.C. 154(b) by 192 days.

This patent is subject to a terminal disclaimer.

(21) Appl. No.: 17/972,361

(22) Filed: Oct. 24, 2022

(65) Prior Publication Data
US 2023/0139576 A1 May 4, 2023

Related U.S. Application Data

(63) Continuation of application No. 16/688,276, filed on Nov. 19, 2019, now Pat. No. 11,478,259, which is a continuation of application No. 15/606,643, filed on May 26, 2017, now Pat. No. 10,478,200, which is a continuation of application No. 12/762,948, filed on Apr. 19, 2010, now Pat. No. 9,662,126.

(60) Provisional application No. 61/170,290, filed on Apr. 17, 2009.

(51) Int. Cl.
*A61B 17/16* (2006.01)
*A61F 2/40* (2006.01)
*A61F 2/30* (2006.01)

(52) U.S. Cl.
CPC ........ *A61B 17/1684* (2013.01); *A61F 2/4081* (2013.01); *A61F 2002/30233* (2013.01); *A61F 2002/30818* (2013.01); *A61F 2002/30879* (2013.01); *A61F 2002/30881* (2013.01); *A61F 2002/30884* (2013.01); *A61F 2230/0069* (2013.01)

(58) Field of Classification Search
CPC ....... A61B 17/16; A61B 17/1684; A61F 2/40; A61F 2/4081; A61F 2/30
See application file for complete search history.

(56) References Cited

U.S. PATENT DOCUMENTS

| | | | | |
|---|---|---|---|---|
| 6,245,074 B1 * | 6/2001 | Allard | ................ | A61B 17/1684 606/80 |
| 9,662,126 B2 * | 5/2017 | Sikora | .................. | A61F 2/4081 |
| 2006/0058809 A1 * | 3/2006 | Zink | .................. | A61B 17/1684 606/102 |

(Continued)

*Primary Examiner* — Christopher J Beccia
(74) *Attorney, Agent, or Firm* — Grossman, Tucker, Perreault & Pfleger, PLLC

(57) ABSTRACT

The present disclosure relates to a system and method for repairing an articular surface. A guide pin may be secured to an articular surface of a glenoid, wherein the guide pin defines a working axis and the working axis is positioned at an angle α relative to the articular surface, wherein angle α is less than or equal to 90 degrees. An excision device may be advanced over the guide pin, wherein the excision device includes a cannulated shaft and at least one cutter, wherein the at least one cutter is generally aligned in a single plane. A generally hemi-spherical excision site may be formed with the excision device within the articular surface of the glenoid.

20 Claims, 13 Drawing Sheets

(56) References Cited

U.S. PATENT DOCUMENTS

2006/0074430 A1\* 4/2006 Deffenbaugh ........ A61F 2/4612
606/87

\* cited by examiner

GLENOID RESURFACING SYSTEM AND METHOD

CROSS-REFERENCE TO RELATED APPLICATIONS

This application is a continuation of U.S. patent application Ser. No. 16/688,276, (now U.S. Pat. No. 11,478,259) filed Nov. 19, 2019, which is a continuation of U.S. patent application Ser. No. 15/606,643, (now U.S. Pat. No. 10,478,200) filed May 26, 2017, which is a continuation of U.S. patent application Ser. No. 12/762,948, (now U.S. Pat. No. 9,662,126), filed Apr. 19, 2010 which claims the benefit of U.S. Provisional Patent Application Ser. No. 61/170,290, filed on Apr. 17, 2009. The entire disclosures of all of the above listed applications are incorporated herein by reference.

FIELD

This disclosure relates to devices and methods for the repair of defects that occur in articular cartilage on the surface of bones, particularly the shoulder.

BACKGROUND

Articular cartilage, found at the ends of articulating bone in the body, is typically composed of hyaline cartilage, which has many unique properties that allow it to function effectively as a smooth and lubricious load-bearing surface. When injured, however, hyaline cartilage cells are not typically replaced by new hyaline cartilage cells. Healing is dependent upon the occurrence of bleeding from the underlying bone and formation of scar or reparative cartilage called fibrocartilage. While similar, fibrocartilage does not possess the same unique aspects of native hyaline cartilage and tends to be far less durable.

In some cases, it may be necessary or desirable to repair the damaged articular cartilage using an plant. While implants may be successfully used, the implant should have a shape substantially corresponding to the articular cartilage proximate the area where the implant is to be placed in order to maximize the patient's comfort, minimize damage to surrounding areas, and maximize the functional life of the implant.

BRIEF DESCRIPTION OF DRAWINGS

The above-mentioned and other features of this disclosure, and the manner of attaining them, may become more apparent and better understood by reference to the following description of embodiments described herein, taken in conjunction with the accompanying drawings, wherein.

DETAILED DESCRIPTION

According to one embodiment, the present disclosure may feature a system d method for resurfacing at least a portion of articular surface having a defect by replacing a portion of the articular surface with an implant. The implant may comprise a load bearing surface having a contour and/or shape substantially corresponding to the patient's original articular surface about the defect site which may be configured to engage an adjacent articular surface. The present disclosure will describe a system and method for replacing a portion of the articular surface of the glenoid; however, it should be understood that the system and method according to the present disclosure may also be used to resurface articular surfaces other than the glenoid.

As an initial matter, many of the devices described herein comprise cannulated components configured to be arranged over other components. The degree to which the cannulated, passageway (i.e., internal diameter of the passageway/cavity) of a first component corresponds to the external diameter of the component over which it is being placed may be close enough to generally eliminate excessive movement. Excessive movement may be defined as an amount of movement that may result in surgically relevant misalignment of the implant relative to the articular surface.

Figure 1:
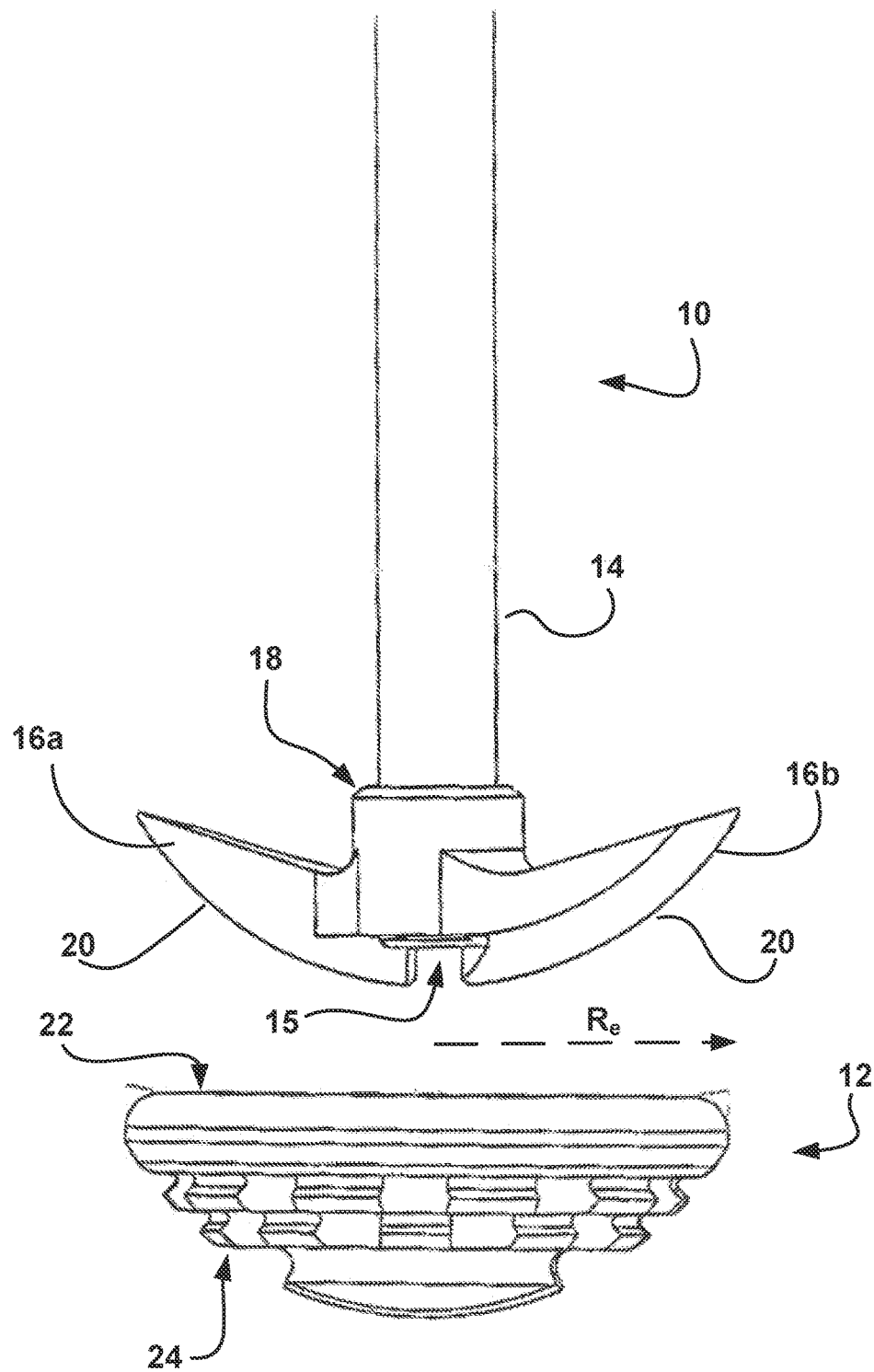
FIG. 1 illustrates a side view of an example of an excision device and an plant.

Referring now to FIG. 1 one embodiment of an excision device 10 and an implant 12 are generally illustrated. As will be explained in greater detail herein, the excision device 10 tray be configured to form an implant or excision site within the articular surface (e.g., the glenoid) configured to receive at least a portion of the implant 12. The implant 12 may be configured to replace the articular surface in an area proximate one or more defects. The system and method consistent with the present disclosure may repair a defect on the articular surface of a glenoid without having to replace the entire glenoid.

Accordingly to at least one embodiment, the implant 12 may be configured to replace only a portion of the articular surface proximate the defect site rather than the entire articular surface. As such, the implant 12 may minimize the amount of the articular surface which is operated on thus allowing more of the patient's original articular surface to be unaffected and providing a more physiologically normal joint. The system and method consistent with one embodiment of the present disclosure may allow for "key-hole"

surgery in which a minimum number and size of incisions are made. As may be appreciated, "key-hole" surgery may reduce the amount of pain and/or discomfort experienced by the patient and, may reduce healing times.

The excision device 10 may include a cannulated shaft 14 defining a passageway 15 configured to be received over at least a portion of a guide pin or the like (not shown). The excision device 10 may also include at least one cutter 16 a, 16 b extending radially outwardly and away from a distal end 18 of the shaft 14. Each cutter 16 a, 16 b may have a cutting surface 20 configured to create a hemispherical implant site, i.e., an excision site to receive the implant. For example, the cutting surface 20 may have a generally arcuate shape which sweeps towards the proximal end of the shaft 14 as the radius $R_e$ from the shaft 14 increases on the cutter 16 a, 16 b. It may be appreciated that the hemi-spherical excision site may exhibit some degree of deviation and the hemi-spherical excision site may be, in some examples, teardrop shaped or pyriform.

The contour of the cutting surfaces 20 may define the contours of the excision site as the cutters 16 a, 16 b are rotated about the central axis of the excision site. While the cutting surfaces 20 are illustrated having a generally constant arc or curvature, the cutting surfaces 20 may include one or more protrusions and/or recesses configured to create a corresponding radial groove and/or lips/protrusions within the excision site. These radial grooves and/or lips/protrusions on the cutting surfaces 20 may facilitate alignment of the implant 12 and/or may increase the mechanical coupling of the implant 12 within the excision site.

Figure 2:
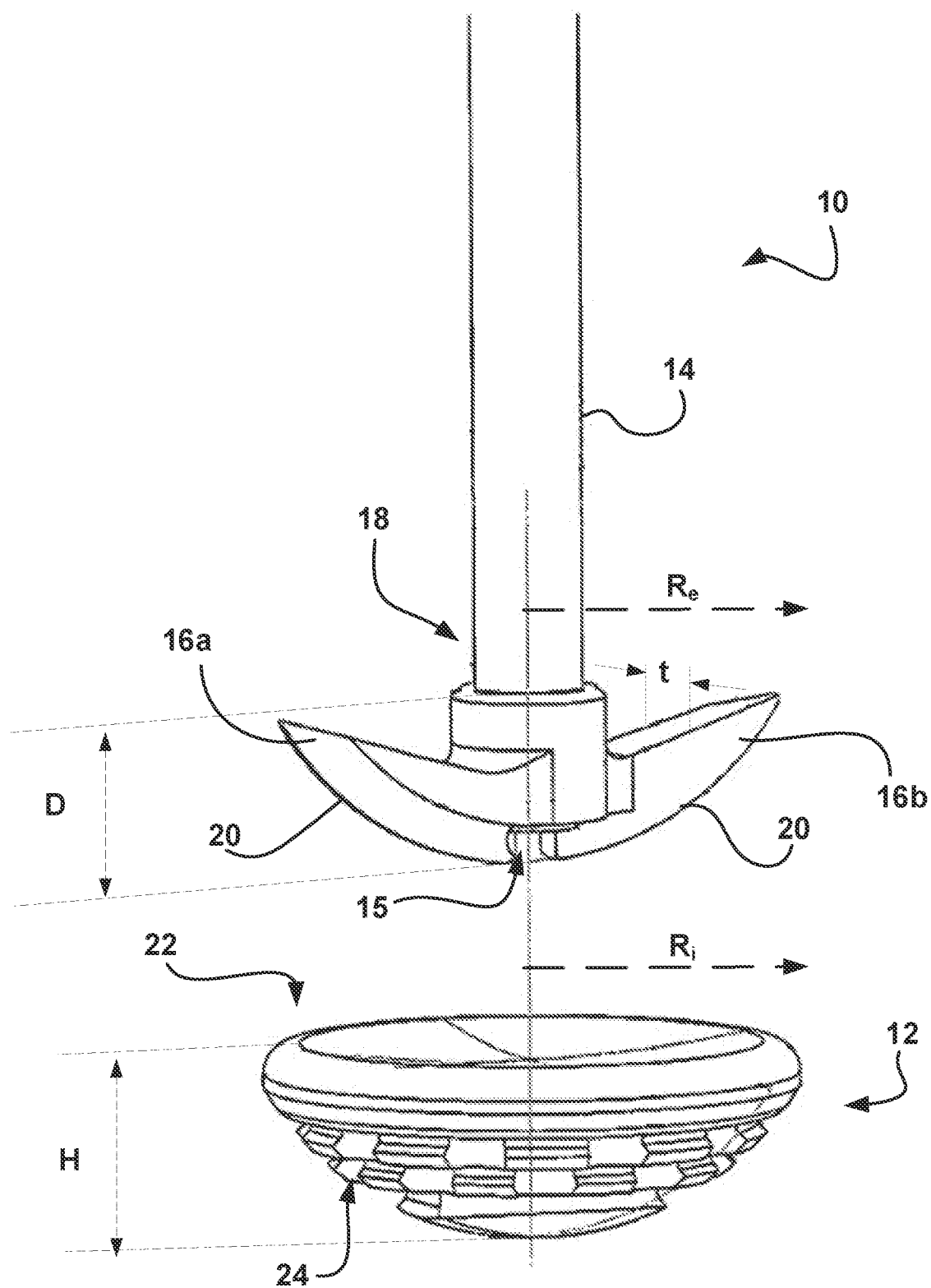
FIG. 2 illustrates a perspective view of an example of an excision device and an implant.

Turning now to FIG. 2, the overall radius $R_e$ of the cutters 16 a, 16 b may define the radius of the implant site created by the excision device 10 within the articular surface and may also substantially correspond to the radius $R_i$ of the implant 12. In addition, the depth D of the cutters 16 a, 16 b may also define the height of the excision site created by the excision device 10 and may also substantially correspond to the height H of the implant 12. For example, the overall radius $R_e$ of the cutters 16 a, 16 b may be between 7.0 mm to 20.0 mm, for example, 7.0 mm to 15.0 mm and/or 10.0 mm, to 12.5 mm (including all values and ranges therein) and the depth D may be between 4.0 mm to 10.0 mm, for example, 5 mm (including all values and ranges herein).

According to at least one embodiment, the excision device 10 may include a first and a second cutter 16 a, 16 b which may be disposed approximately 180 degrees relative to each other. For example, the cutters 16 a, 16 b may extend generally radially outwardly from the shaft about a first and a second generally opposite side of the distal end 18 of the shaft 14. The cutters 16 a, 16 b may also have a generally slim profile configured to be disposed between two adjacent articular surfaces as explained further herein. For example, the cutters 16 a, 16 b may have a cross-sectional thickness (t) of 0.5 mm to 3.0 mm, for example, 2.0 mm (including all values and ranges therein). In one embodiment the at least one cutter may provide a generally hemispherical excision site regardless of the angle which the guide pin is disposed relative to the articular surface 54.

Figure 3:
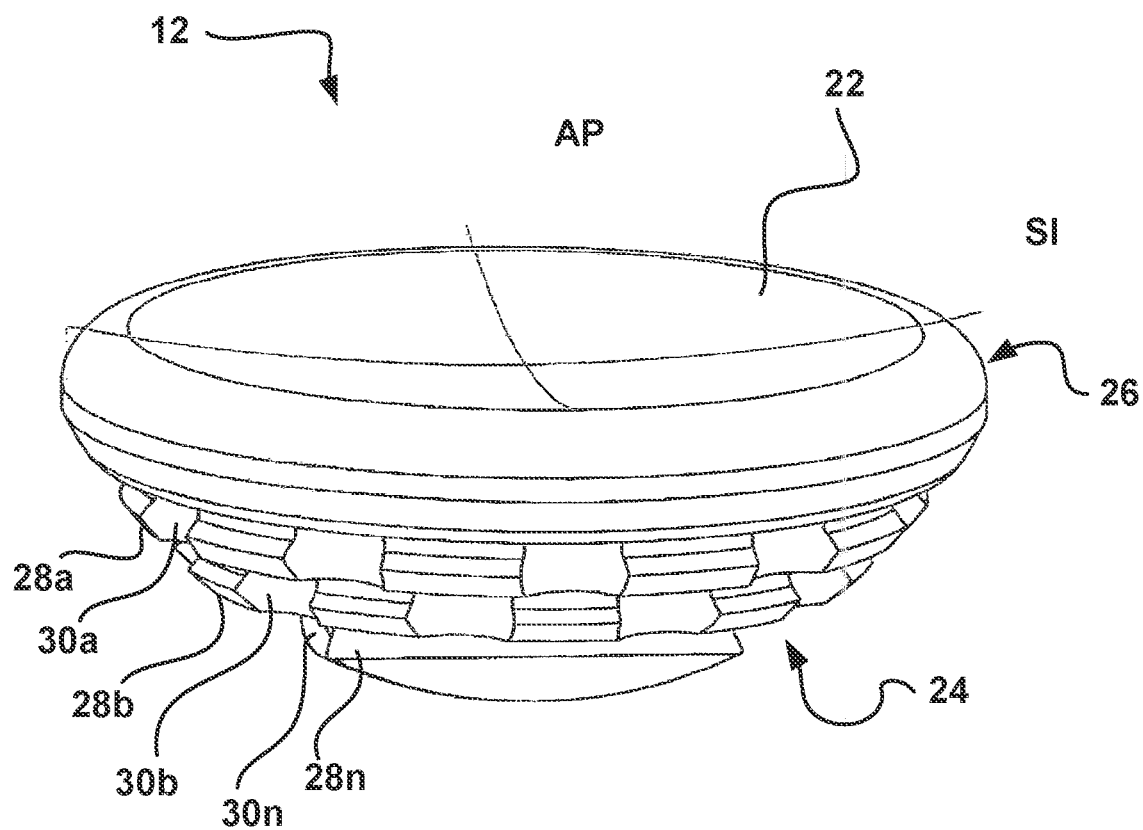
FIG. 3 illustrates an example of an implant.

The implant 12 may include a load bearing surface 22 and a bone facing surface 24. Turning now to FIG. 3, a top perspective view of an implant 12 consistent with at least one embodiment herein is generally illustrated. The load bearing surface 22 may have a contour substantially corresponding to or based on the contour of the patient's articular surface being replaced (i.e., the articular surface which is removed by the excision device 10). The contour of the load bearing surface 22 may be based on a plurality of measurements taken at the patient's articular surface (for example, using a measuring and/or mapping tool as generally described in U.S. Pat. Nos. 6,520,964, 6,610,067, 6,679,917, 7,029,479 and 7,510,558, which are fully incorporated herein by reference) and/or may be based on one or more templates.

The load bearing surface 22 may be based on two or more curvatures, for example, the anterior-posterior (AP) curvature and the superior-inferior (SI) curvature. One or more of the AP and/or SI curvatures may themselves be based on multiple curves, (for example, as generally described in U.S. patent application Ser. No. 12/027,121, filed Feb. 6, 2008 and entitled SYSTEM AND METHOD FOR JOINT RESURFACE REPAIR, which is fully incorporated herein by reference). The load bearing surface 22 may be generally concaved. For example, the load bearing surface 22 may have a generally hemi-spherical shape.

The load bearing surface 22 may also include a beveled region 26 disposed about the perimeter of the load bearing surface 22. The beveled region 26 may reduce the potential of further damage to the surrounding articular surface by eliminating a hard transition between the load bearing surface 22 and the remaining articular surface. The beveled region 26 may be particularly helpful if a portion of the implant 12 is slightly proud with respect to the remaining articular surface.

The bone facing surface 24 may be configured to be generally received in the excision site created by the excision device 10. For example, the bone facing surface 24 may have a generally hemi-spherical shape substantially corresponding to the contour of the cutting surfaces 20 of the cutters 16 a, 16 b. The bone facing surface 24 may also include one or more lips, protrusions, ribs or the like 28a-28n configured to increase the mechanical connection between the implant 12 and the patient's bone within the excision site. Again, these lips or the like 28a-28n may generally correspond to the contours of the cutting surfaces 20 of the cutters 16 a, 16 b. The voids or space 30a-30n between the lips 28a-28n may create pockets for bone in-growth and/or bone cement.

Figure 4:
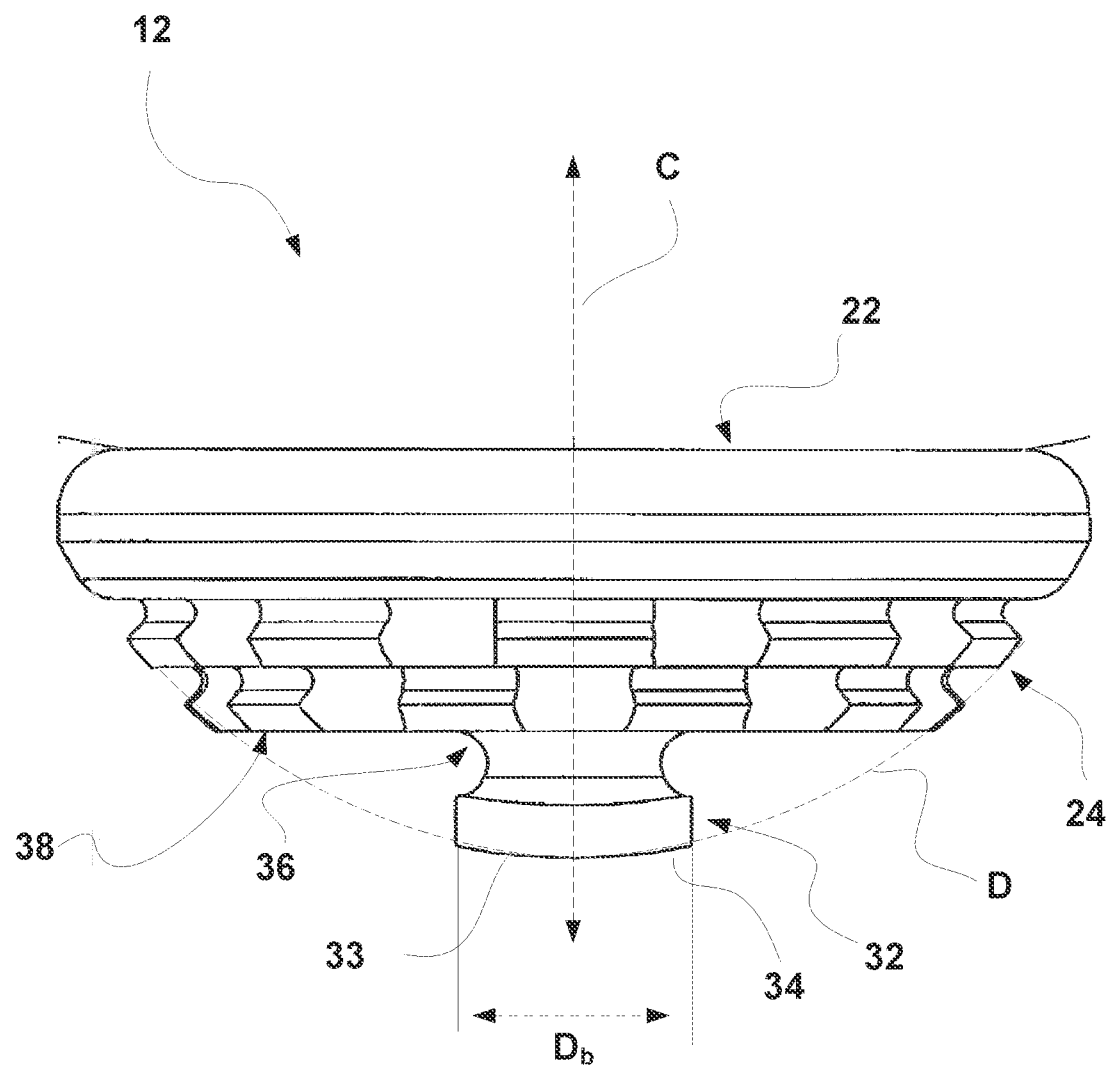
FIG. 4 illustrates a side view of an example of an implant.
Figure 5:
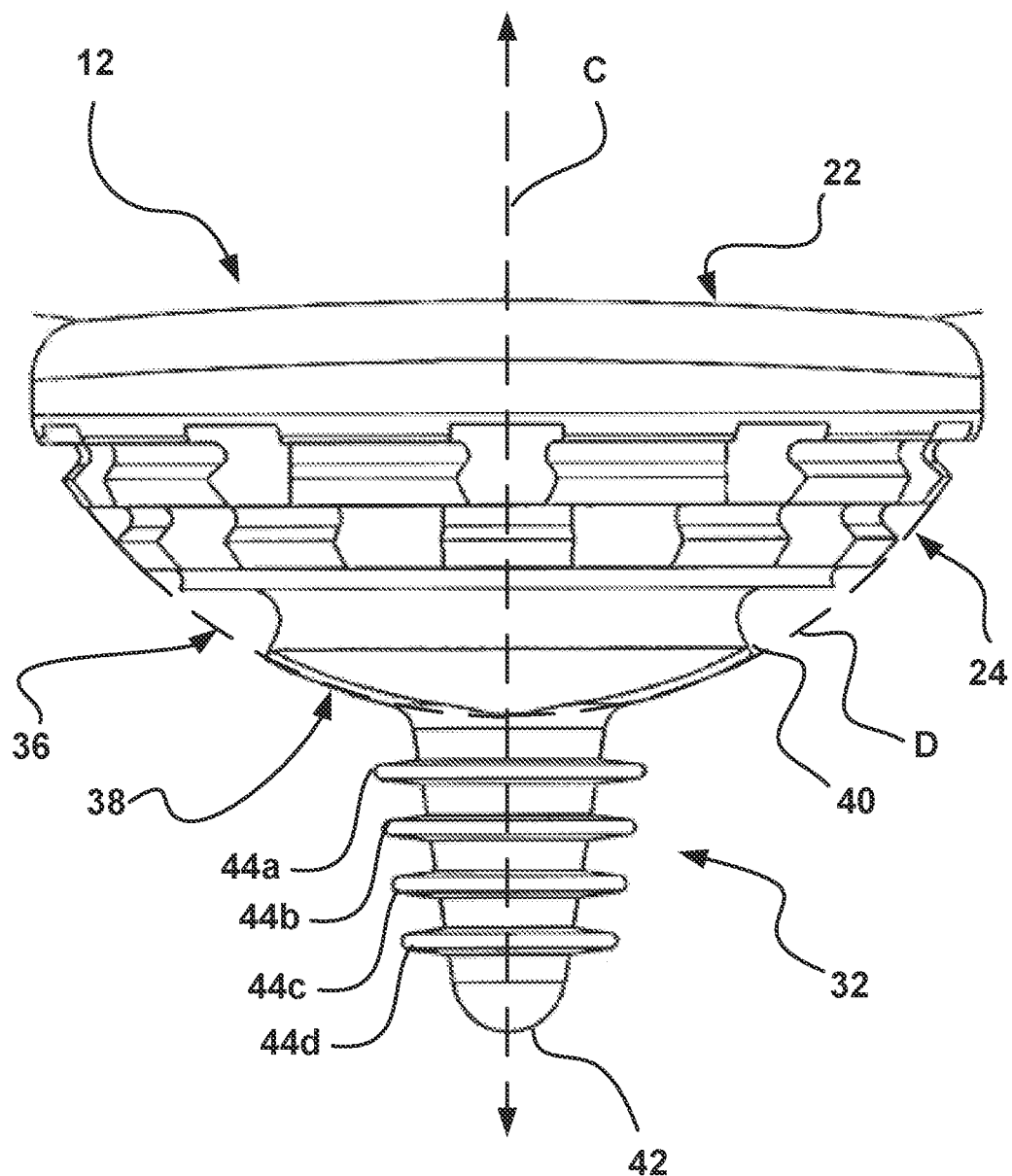
FIG. 5 illustrates a side view of another example of an implant.

Turning now to FIGS. 4 and 5, the implant 12 may optionally include at least one keel or tail 32 extending generally outwardly from the bone facing surface 24. For example, the implant 12 may include at least one keel 32 including a protrusion or button 34 disposed about a distal end of a base region 36 as generally illustrated in FIG. 4. For example, the implant 12 may include a single keel 32 extending generally downwardly and away from the bottom surface 38 of the bone facing surface 24 generally along the central axis C of the implant 12. The base region 36 may be coupled to the bottom surface 38 of the bone facing surface 24 and may have an hour-glass shape which may initially taper radially inwardly and then taper radially outwardly. The bottom surface 33 of the button 34 may have a curvature substantially corresponding to the curvature of the implant site. For example, the bottom surface of the button 34 may have a curvature (generally illustrated by dotted curve D) substantially corresponding to the curvature of the cutting surfaces 20.

The button 34 may extend generally radially outwardly from a distal end of the base region 36. As such, the button 34 may have a diameter $D_b$ greater than at least a portion of the base region 36, for example, the portion of the base region adjacent to the button 34. According to one embodiment, the diameter $D_b$ of the button 34 may be the same as or slightly larger than the diameter of the cavity in the excision site in which it is configured to be received. As such, the button 34 may form an interference fit with the cavity in the excision site which may secure the implant 12 to the bone and may also facilitate alignment of the implant 12 with respect to the articular surface and the excision site. Alternatively, the diameter $D_b$, of the button 34 may be slightly smaller than the diameter of the cavity in which it is configured to be received. As such, the button 34 may also facilitate alignment of the implant 12 with respect to the articular surface and the excision site. In addition, bone cement or the like may be disposed around the keel within the cavity to increase the mechanical connection between the keel 32 and the bone.

FIG. 5 illustrates another embodiment of a keel 32. The keel 32 may include a base region 36 extending generally outwardly/downwardly and away from the bottom surface 38 of the bone facing surface 24 generally along the central axis C of the implant 12. For example, the keel 32 may extend outwardly/downwardly and away from the bottom surface 38 of the bone facing surface 24 beyond the curvature D substantially corresponding to the curvature of the cutting surfaces 20. The keel 32 may be configured to be received in an additional cavity, pocket or the like formed within the excision site. The additional cavity may be formed subsequent to the formation of the excision site using an additional cutter, chisel, drill or the like (not shown).

The base region 36 may include one or more radial lips, grooves, protrusions or the like 40. The keel 32 may also include a protrusion 42 extending generally downwardly and away from the base portion 36 generally along the central axis C of the implant 12. The protrusion 42 may include one or more radial lips, grooves, protrusions or the like 44a-44n. As discussed herein, the keel 32 may be configured to engage a cavity or the like disposed within the excision site and may be configured align the implant 12 with respect to the articular surface and/or the excision site a d may also increase the mechanical coupling of the implant 12 to the bone.

While the keels 32 illustrated in FIGS. 4 and 5 are shown having a generally concentric shape, the keel 32 may have other configurations. For example, the keel 32 may have a shape configured to prevent rotations of the implant 12 with respect to the articular surface. The keel 32 may have a non-circular shape configured to be received in the excision site in a lock-and-key configuration. By way of example, the keel 32 may have a generally multifaceted geometry (such as, but not limited to, rectangular, pentagonal, hexagonal or the like) configured to received in the excision site. The implant 12 and the keel 32 may be a single, integral or unitary component car may be formed from two or more pieces which may be secured to each other (either permanently or removably secured).

Turning no to FIGS. 6-10, one method of installing an implant 12 consistent with the present disclosure is generally illustrated. One or more incisions 49 may be created proximate the patient's shoulder 50 to provide access to the defect 52 on the patient's articular surface 54, for example, using a scalpel or the like. The incision 49 may be made through the anterior portion of the patient. Again, the present disclosure will describe a system and method for replacing a portion of the articular surface of the glenoid; however, it should be understood that the system and method according to the present disclosure may also be used to resurface articular surfaces other than the glenoid. The system and method consistent with one embodiment of the present disclosure may allow for "key-hole" surgery in which a minimum number and size of incisions are made. As may be appreciated, "key-hole" surgery may reduce the amount of pain and/or discomfort experienced by the patient and may reduce healing times.

Figure 6:
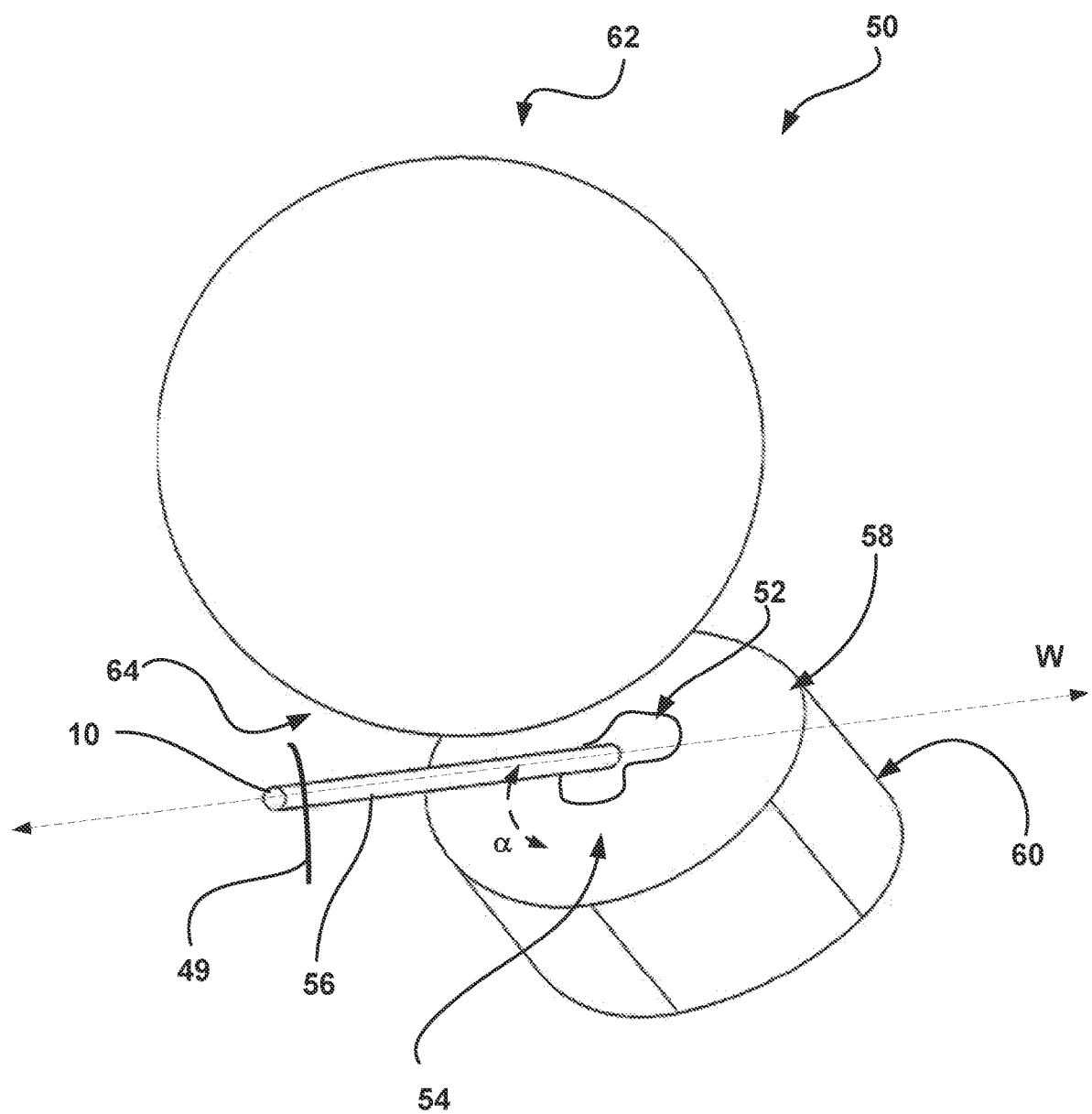
FIG. 6 illustrates an example of a guide pin positioned in the glenoid surface of a scapula.

Once the incision is created, a guide pin 56, FIG. 6, may be positioned about the glenoid 58 on the scapula 60 to provide an access passageway to the glenoidal articular surface 54 as will be described herein. Consistent with one embodiment, the guide pin 56 may comprise threaded and/or self-tapping tip (not shown) configured to be secured to the patient's bone. The guide pin 56 may be secured to the bone using a drill or the like (not shown) and at least a portion of which may be disposed proximate to and/or within the defect site 52 on the articular surface 54. Optionally, a drill guide (not shown) may be used to facilitate alignment of the guide pin 56 with respect to the articular surface 54.

The guide pin 56 may be disposed along a longitudinal or working axis (W) at an angle α relative to the articular surface 54. Angle α may be less than or equal to 90 degrees, wherein α≤90 degrees with respect to the articular surface 54. In some examples, angle α may be less or equal to 90 degrees and greater than or equal to 45 degrees with respect to the articular surface 54, wherein 45 degrees≤α≤90 degrees with respect to the articular surface 54. In further examples, 90 degrees>α>45 degrees and/or 90 degrees>α≥45 degrees, with respect to the articular surface 54. The degree of the angle α may depend on the location and/or size of the defect 52 and may be selected to avoid contact with the humerus 62. In some circumstances the degree of the angle α may also be selected to avoid contact with the perimeter of the articular surface 54.

Figure 7:
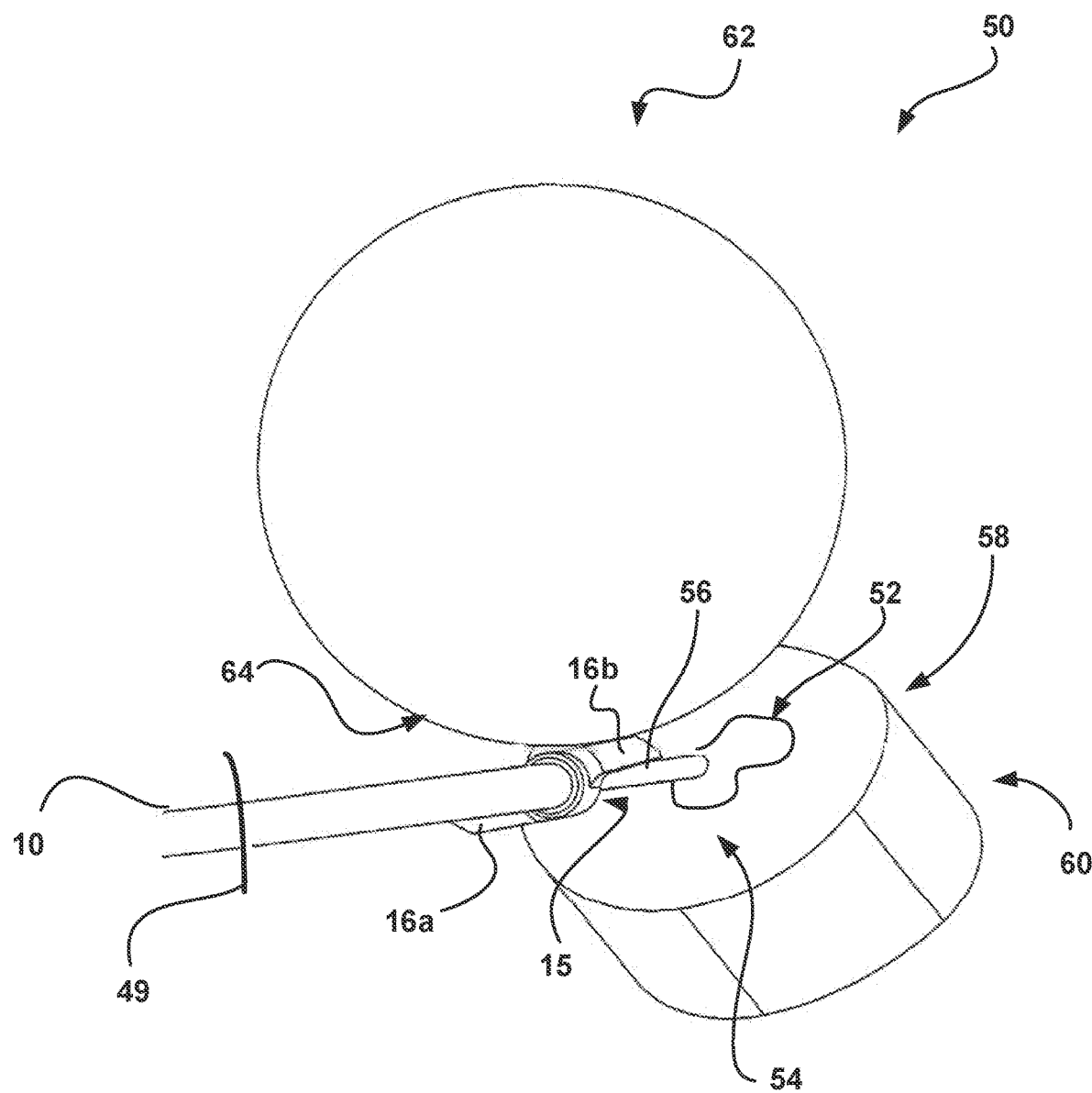
FIG. 7 illustrates an example of an excision device including a cannulated shaft and a cutter positioned at the distal end of the cannulated shaft passing over the guide pin positioned in the glenoid surface of a scapula.
Figure 8:
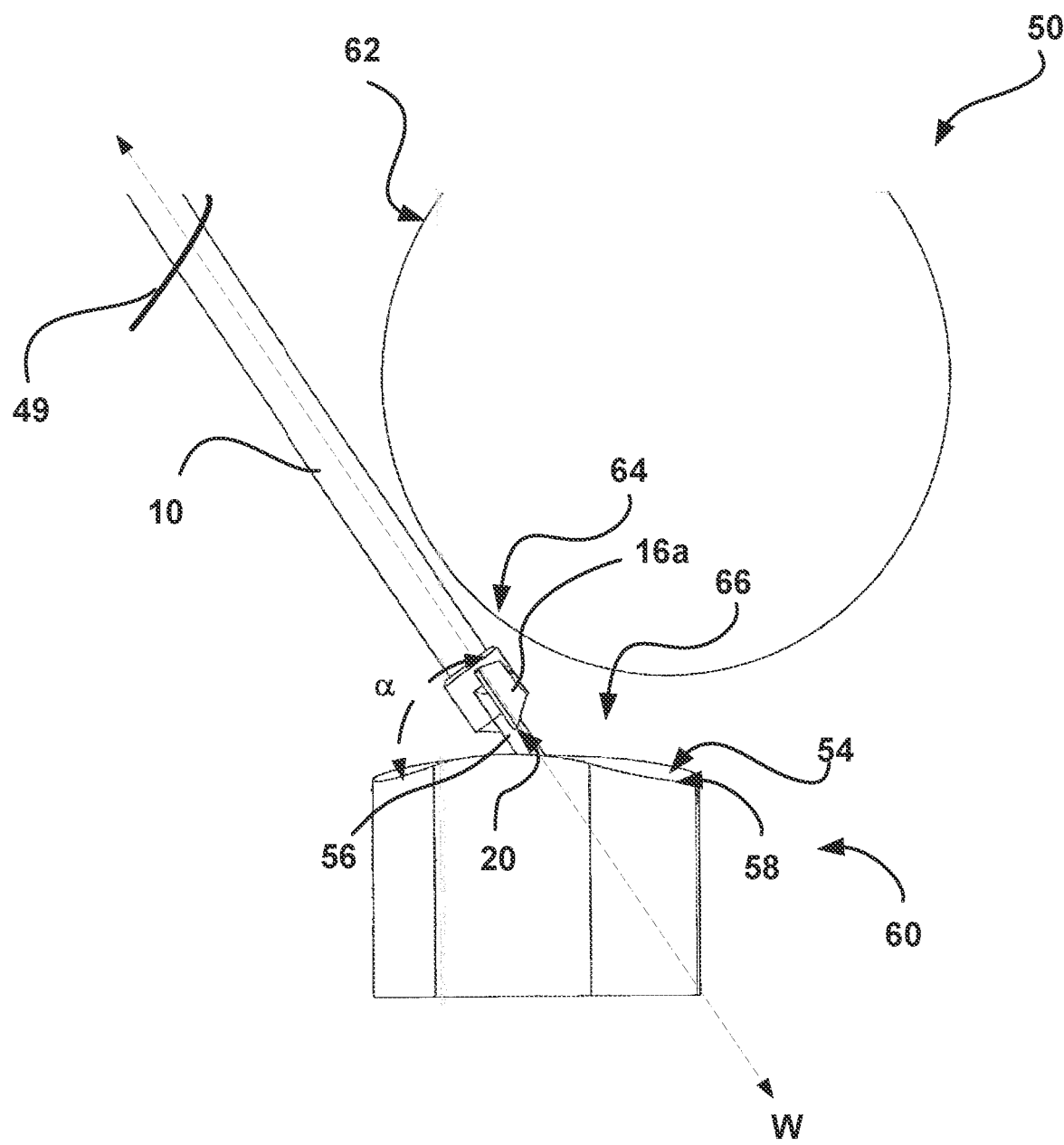
FIG. 8 illustrates a side view of an example of an excision device including a cannulated shaft and a cutter positioned at the distal end of the cannulated shaft passing over the wide pin positioned in the glenoid surface of a scapula.

Once the guide pin 56 is secured to the articular surface 54, the excision device 10 may be advanced over the guide pin 56 as generally illustrated in FIG. 7. For example, the guide pin 56 may be received within the passageway 15 defined by the cannulated shaft 14. According to at least one embodiment, the cutters 16 a, 16 b may be generally aligned in a single plane extending along the longitudinal axis of the excision device 10. The plane of the cutters 16 a, 16 b may be orientated generally tangential to the articular surface 64 of the humerus 62 such that the cutters 16 a, 16 b may slide by the articular surface 64 of the humerus 62 and between the humerus 62 and the scapula 60 as generally illustrated in FIGS. 7 and 8.

Once the cutters 16 a, 16 b are advanced oven: the guide pin 56 to the articular surface 54, the excision device 10 may be rotated about the guide pin 56. As may be best seen in FIG. 8, a pocket of cavity 66 may be present between the articular surface 54 of the glenoid 58 and the articular surface 64 of the humerus 62. The cutters 16 a, 16 b of the excision device 10 tray therefore rotate about the guide pin 56 without contacting the articular surface 64 of the humerus 62.

Figure 9:
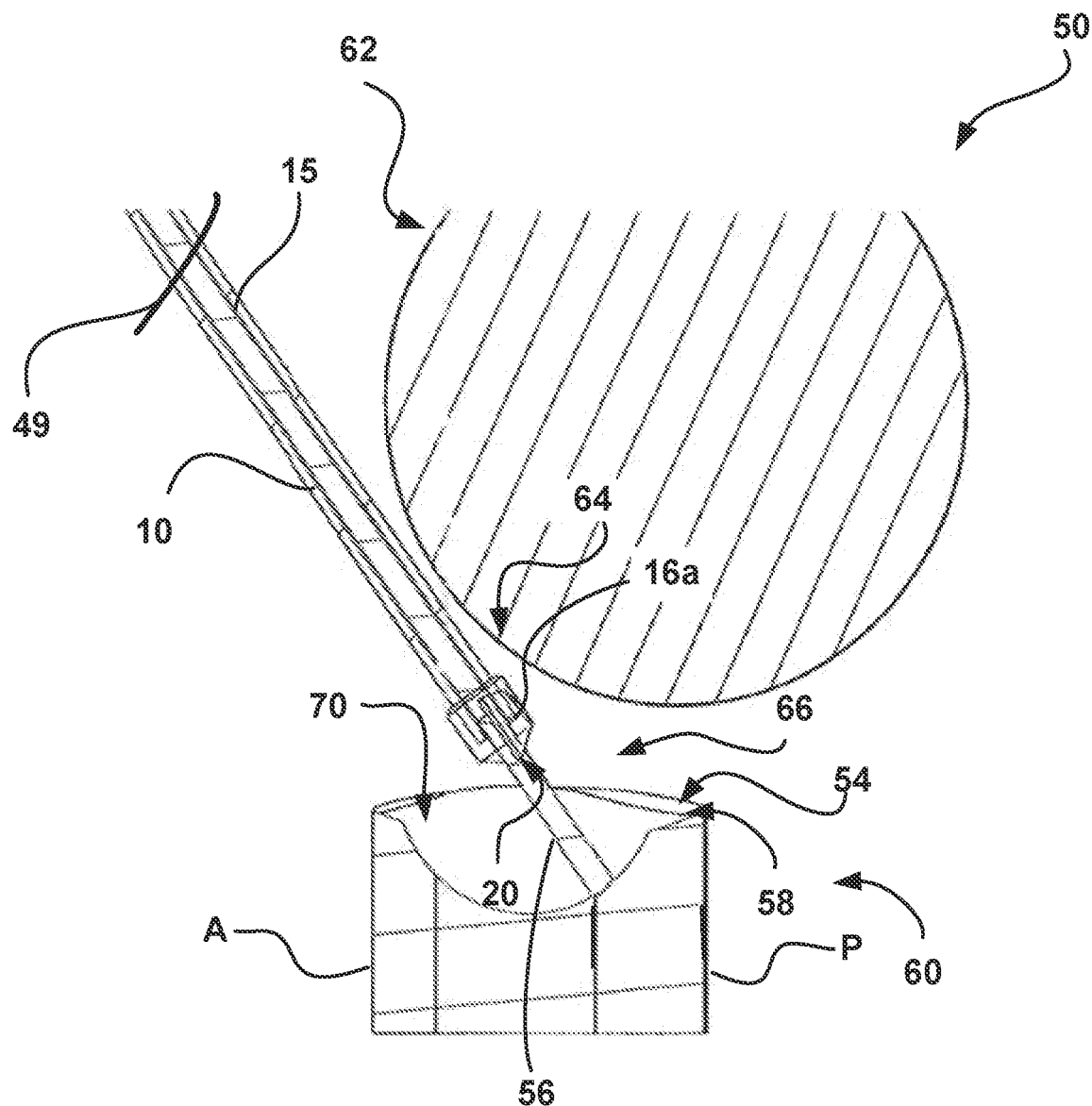
FIG. 9 illustrates a side-cross sectional view of an excision device including a cannulated shaft and a cutter positioned at the distal end of the cannulated shaft passing over the guide pin positioned in the glenoid surface of a scapula.

The excision device 10 may thus be rotated about the guide pin 56 to form an excision site 70 within the articular surface 54 of the glenoid 58 as generally illustrated in FIG. 9. Due to the contour of the cutting surfaces 20 of the cutters 16 a, 16 b, the excision site 70 created by the excision device 10 may have a generally hemi-spherical configuration regardless of the angle α of the guide pin 56.

Figure 10:
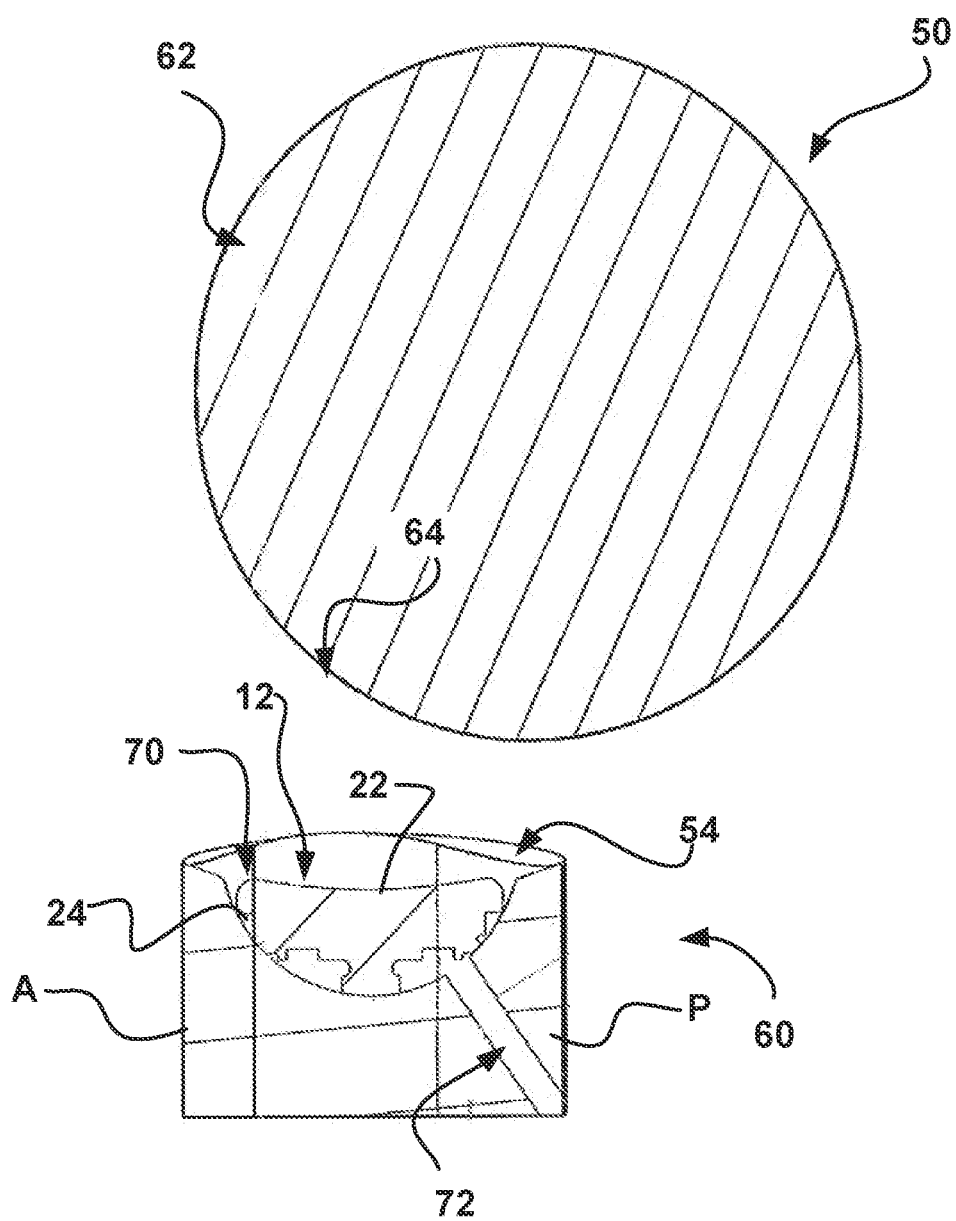
FIG. 10 illustrates a side-cross sectional view of an excision site including an implant.

Once the excision site 70 is formed within the articular surface 54, the excision device 10 and the guide pin 56 may be removed as generally illustrated in FIG. 10. The removal of the guide pin 56 may leave a cavity 72 formed by the distal tip of the guide pin 56. The implant 12 may then be received in the excision site 70. The spherical configuration of the excision site 70 may normalize the implant 12 with respect to the remaining articular surface 54. The load bearing surface 22 of the implant 12 may substantially match the original contour of the patient's articular surface 54 which was removed.

Figure 11:
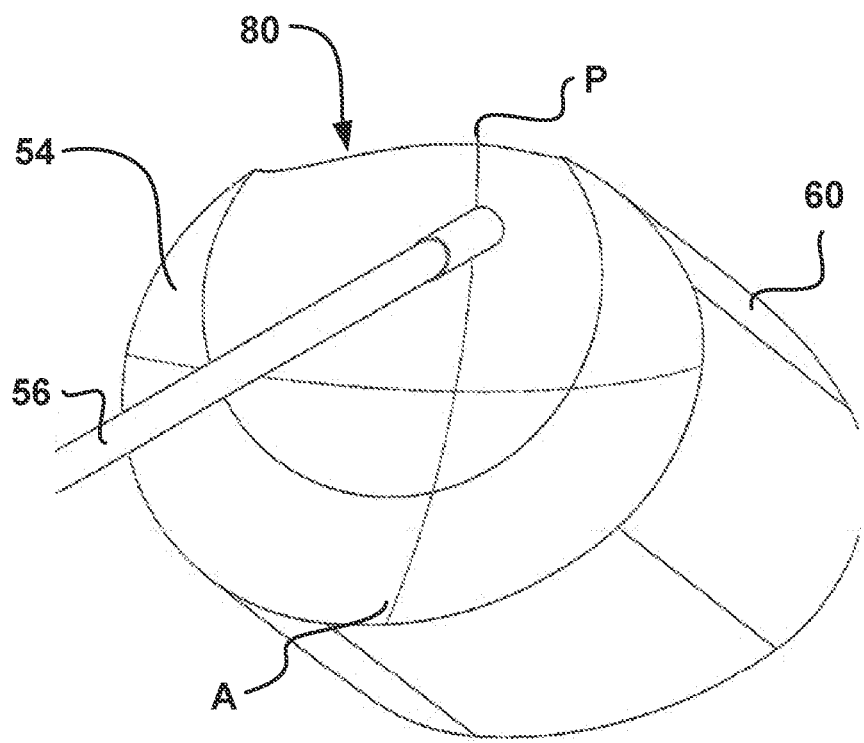
FIG. 11 illustrates an example wherein a portion of the perimeter of the articular surface is damaged and the guide pin is positioned such that a repair nay be made at or near the perimeter of the articular surface.

As illustrated in FIG. 11, the system and method according to the present disclosure may also repair a defect 80 on the articular surface 54 in which a portion of the perimeter of the articular surface 54 is damaged or missing. For example, the posterior portion P of the articular surface 54 may have a defect 80, wherein a portion of the perimeter of the articular surface 54 is missing which may be caused by advanced chronic shoulder dislocation and/or early onset arthritis. To repair a defect 80 proximate the perimeter of the articular surface 54, the guide pin 56 may be moved further towards the posterior end P of the articular surface 54. The exact location of the guide pin 56 with respect to the articular surface 54 may depend on the location and size of the defect 80 as well as the size of the cutters 16 a, 16 b of the excision device 10.

Figure 12:
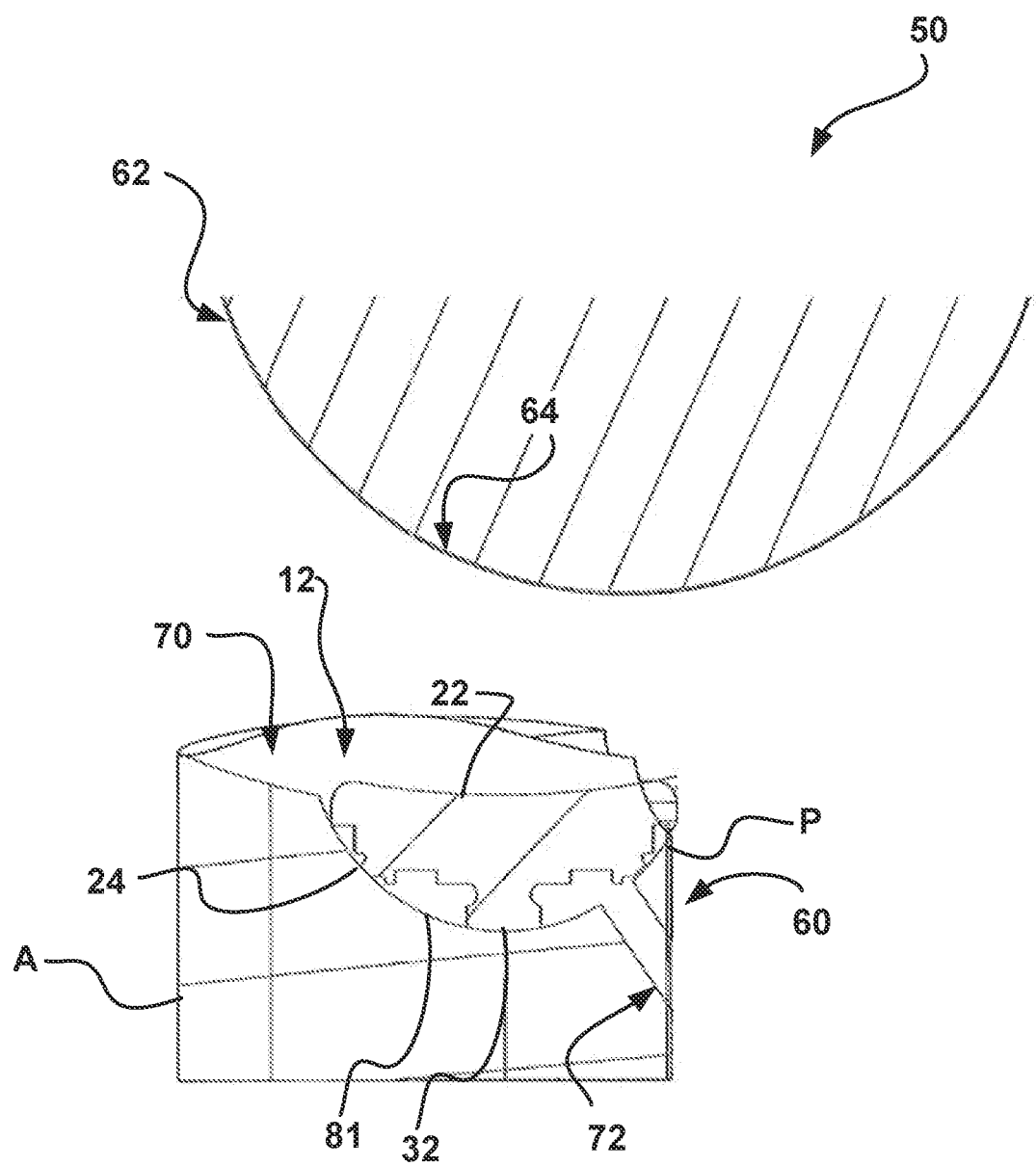
FIG. 12 illustrates a side-cross sectional view of pan excision site including an example of an implant positioned at or near the perimeter of the articular surface.

According to one embodiment, the guide pin 56 may be located a distance away from the perimeter of the articular surface 54 which generally corresponds to the radius $R_e$ of the cutters 16 a, 16 b. The excision device 10 may be advanced over the guide pin 56 and rotated as described herein. Accordingly, the cutters 16 a, 16 b may remove a portion of the articular surface 54 to form an excision site 81 disposed about the perimeter of the articular surface 54 as generally illustrated in FIG. 12. It may be appreciated that in such a manner, the perimeter may intersect a portion of the generally hemispherical excision site 81. The excision device 10 and the guide pin 56 may then be removed and the implant 12 may be received within the excision site 81. As may be seen in FIG. 12, a portion of the implant 12 may replace the perimeter of the articular surface 54 which was damaged and/or missing.

Figure 13:
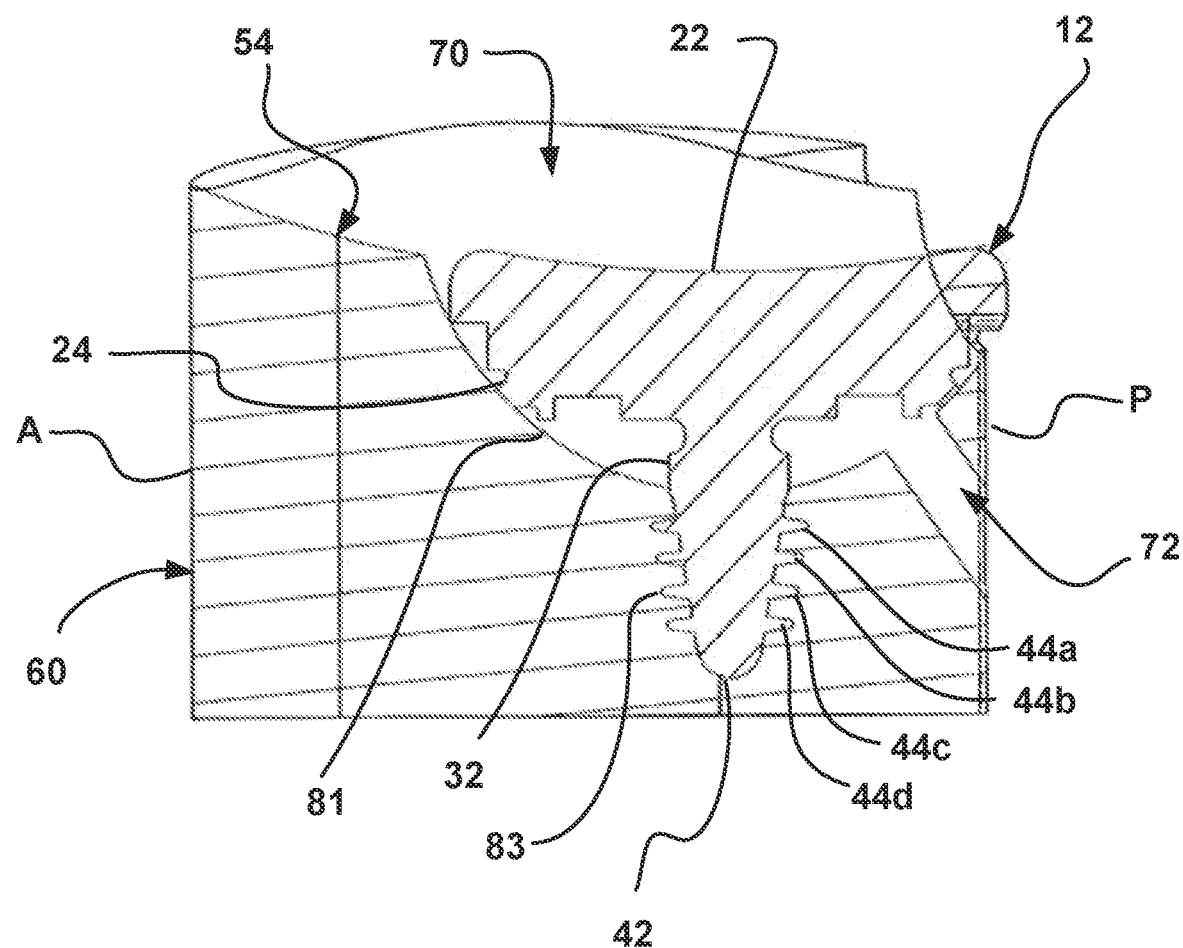
FIG. 13 illustrates an example of a side-cross sectional view of an example of an excision site including an example of an implant positioned at or near the perimeter of the articular surface.

The implant 12 may also include a keel 32 as generally illustrated in FIGS. 12 and 13. The keel 32 may facilitate alignment of the implant 12 with respect to the articular surface 54 and/or may provide an increased mechanical connection between the implant 12 and the bone. As discussed herein, the excision site 81 may also include one or more cavities 83, FIG. 13, configured to received at least a portion of the keel 32 (for example, but not limited to, one or more radial lips 44a-44n of the protrusion 42.

Once the position/orientation of the implant 12 has been confirmed (i.e., the contour of the load bearing surface 22 has been confirmed along the AP and/or SI planes to generally correspond to the original contour of the articular surface), the implant 12 may be secured to the bone. The implant 12 may be held in place by the lips, protrusions, ribs or the like 28a-28n of the bone facing surface 24, the keel 32, and/or bone cement or the like.

Accordingly, in one embodiment, the present disclosure is directed to a method of repairing an articular surface, wherein the method may include securing a guide pin to an articular surface of a glenoid, wherein the guide pin may define a working axis and the working axis is positioned at an angle α relative to the articular surface, wherein angle α is less than or equal to 90 degrees. It may be appreciated that n some embodiments the guide pin may be configured to be disposed at an angle α, wherein 90 degrees≥α≥45 degrees relative to the articular surface. In some examples, the articular surface includes a perimeter and the perimeter includes a defect and the excision site extends to the perimeter.

The method may also include advancing an excision device over the guide pin, wherein the excision device nay include a cannulated shaft and at least one cutter. In some embodiments the cutter may generally be aligned in a single plane. In some embodiments, the cutter may include a first cutter and a second cutter, which extend generally radially outwardly from the cannulated shaft at an angle of approximately 180 degrees from each other. In other embodiments, the cutter may have a cross-sectional thickness of 0.5 mm to 3.0 mm.

The method may also include forming a generally hemi-spherical excision site with the excision device within the articular surface of the glenoid. In some embodiments, the generally hemi-spherical excision site may be formed by rotating the at least one cutter about the guide pin. In addition, the method may also include removing the guide pin and placing an implant in the excision site.

In another aspect, the present disclosure relates to a method of repairing an articular surface. The method may include creating an incision through an anterior surface of a patient proximate to the patient's shoulder, as may be appreciated the shoulder includes a glenoid including a first articular surface and a humerus including a second articular surface. The method may also include inserting a guide pin through the incision at an angle to avoid contact with the second articular surface. The method may further include securing the guide pin to the first articular surface, wherein the guide pin may be positioned at an angle α relative to the first articular surface, and angle α may be less than or equal to 90 degrees. In addition, the method may include advancing an excision device over the guide pin, wherein the excision device may include a cannulated shaft and at least one cutter. In some embodiments, the cutter may extend away from the cannulated shaft and exhibit a thickness of 0.5 mm to 3.0 mm. In further embodiments, the cutter may be oriented generally tangentially to the second articular surface avoiding contact with the humerus as the excision device is advanced over the guide pin. The method may also include forming a generally hemi-spherical excision site in the first articular surface with the excision device by rotating the at least one cutter without contacting the second articular surface.

A further aspect of the present disclosure relates to a system for repairing an articular surface. The system may include a guide pin configured to be secured into bone beneath the articular surface of a glenoid. In some embodiments, the guide pin may be configured to be disposed at an angle α relative to the articular surface, wherein angle α is <90 degrees. In further embodiments, the guide pin may be configured to be disposed at an angle α relative to the articular surface, wherein 90 degrees≥α≥45 degrees.

The system may also include an excision device. The excision device may include a cannulated shaft configured to be advanced over the guide pin, and at least one cutter configured to form a generally hemispherical excision site in the glenoid about the guide pin. In one embodiment, the at least one cutter may have a cross-sectional thickness of 0.5 mm to 3.0 mm. The cutter may also include a cutting surface having a generally arcuate shape sweeping towards a proximal end of the cannulated shaft. The cutting surface may define a contour of the excision site as the excision device is rotated about the cannulated shaft. In another embodiment, the cutter may include a first cutter and a second cutter, wherein the first and second cutters may extend generally radially outwardly from the cannulated shaft at an angle approximately 180 degrees from each other.

The system nay further include an implant. The implant may have a load bearing surface and a bone facing surface, wherein the load bearing surface may exhibit a contour substantially corresponding to the contour of the articular surface and the generally hemi-spherical bone facing surface may be configured to be received in the generally hemi-spherical excision site. In some embodiments, the load bearing surface may include a beveled region disposed about a perimeter of the load bearing surface. In further embodiments, the bone facing surface may include at least one lip, protrusion and/or rib configured to increase a mechanical connection between the implant and bone within the excision site. In yet further embodiments, the implant may also include at least one keel extending generally outwardly from the bone facing surface. In additional embodiments, the at least one keel may include a protrusion disposed about a distal end of a base region. In one embodiment, the implant may include a single keel extending generally downwardly and away frown a bottom surface of the bone facing surface generally along a central axis C of the implant. The base region may be coupled to a bottom surface of the bone facing surface and include an hour-glass shape. In one embodiment, the bottom surface of the keel may include a curvature substantially corresponding to a curvature of the excision site. The bottom surface of the keel may also include a curvature substantially corresponding to a curvature of a cutting surface of the at least one cutter. In some embodiments, the at least one keel may extend outwardly and downwardly from a bottom surface of the bone facing surface beyond a curvature D substantially corresponding to a curvature of a cutting surface of the at least one cutter.

It may be appreciated that in some embodiments, an overall radius $R_e$ of the at least one cutter tray define a radius of the excision site created by the excision device. In addition, in some embodiments, the overall radius $R_e$ may substantially correspond to a radius $R_i$ of the implant. In some embodiments, a depth D of the at least one cutter may define a height of the excision site created by the excision device. In additional embodiments, a depth D may substantially correspond to a height H of the implant.

As mentioned above, the present disclosure is not intended to be limited to a system or method which roust satisfy one or ore of any stated or implied object or feature of the present disclosure and should not be limited to the preferred, exemplary, or primary embodiment(s) described herein. The foregoing description of a preferred embodiment of the present disclosure has been presented for purposes of illustration and description. It is not intended to be exhaustive or to limit the present disclosure to the precise form disclosed. Obvious modifications or variations are possible in light of the above teachings. The embodiment was chosen and described to provide the best illustration of the principles of the present disclosure and its practical application to thereby enable one of ordinary skill in the art to utilize the present disclosure in various embodiments and with various modifications as is suited to the particular use contemplated. All such modifications and variations are within the scope of the present disclosure.

What is claimed is:

1. A system for repairing a defect on a portion of an articular surface of a patient's glenoid, the system comprising:
   an excision device comprising:
   a cannulated shaft having a first open end and a second open end defining a longitudinally disposed passageway therebetween, the passageway configured to be advanced over a guide pin along a working axis, and
   a reamer including at least one cutter configured to extend from the cannulated shaft, the at least one cutter including a cutting surface having a generally arcuate shape sweeping towards a proximal end of the cannulated shaft and configured to form a generally hemispherical excision site in the patient's glenoid when the excision device is rotated about, and advanced over, the guide pin;
   wherein the cutting surface of the cutter further comprises at least one recess configured to form a radial groove in an articular surface of the glenoid; and
   wherein the reamer and the cannulated shaft are configured to be advanced in a space between articular surfaces of the patient's humerus and scapula such that a rotational axis of the excision device is non-perpendicular to the glenoid articular surface.

2. The system of claim 1, further comprising an implant comprising a load bearing surface and a bone facing surface, wherein the load bearing surface exhibits a contour substantially corresponding to the contour of the articular surface and the bone facing surface is configured to be received in the generally hemispherical excision site.

3. The system of claim 2, wherein the implant is at least partially proud with respect to the articular surface.

4. The system of claim 2, wherein the load bearing surface comprises a beveled region disposed about a perimeter of the load bearing surface.

5. The system of claim 2, wherein an overall radius $R_e$ of the at least one cutter defines a radius of the excision site and wherein the overall radius $R_e$ substantially corresponds to a radius $R_i$ of the implant.

6. The system of claim 2, wherein a depth D of the at least one cutter defines a height of the excision site created by the excision device and wherein the depth D substantially corresponds to a height H of the implant.

7. The system of claim 2, wherein the implant comprises at least one keel extending generally outwardly from the bone facing surface.

8. The system of claim 7, wherein the at least one keel further comprises a protrusion disposed about a distal end of a base region.

9. The system of claim 1, wherein the radial groove is configured to facilitate alignment of an implant with the articular surface.

10. The system of claim 1, further comprising at least one protrusion extending from the cutting surface.

11. The system of claim 1, wherein the radial groove is configured to facilitate mechanical coupling of an implant to the articular surface.

12. The system of claim 1, wherein the guide pin is configured to be disposed at an angle α relative to the articular surface, wherein 90 degrees≥α≥45 degrees.

13. The system of claim 1, wherein the recess is configured to form two or more radial lips in the articular surface of the patient's glenoid.

14. The system of claim 13, wherein the two or more radial lips are spaced to create a pocket between each pair of radial lips of the two or more radial lips to facilitate bone growth.

15. The system of claim 13, wherein the two or more radial lips are spaced to create a pocket between each pair of radial lips of the two or more radial lips to facilitate attaching an implant to the articular surface with bone cement.

16. The system of claim 1, wherein an overall radius $R_e$ of the at least one cutter defines a radius of the excision site created by the excision device.

17. The system of claim 1, wherein at least one of the cutters has an overall radius $R_e$ in the range of 7.0 mm to 20.0 mm.

18. The system of claim 1, wherein a depth D of the at least one cutter defines a height of the excision site created by the excision device.

19. The system of claim 1, wherein the at least one cutter has a cross-sectional thickness of 0.5 mm to 3.0 mm.

20. The system of claim 1, further comprising the guide pin configured to be secured into bone beneath the articular surface of the glenoid.

* * * * *